United States Patent
Loyd et al.

(10) Patent No.: US 10,653,500 B2
(45) Date of Patent: May 19, 2020

(54) SYSTEM AND METHOD FOR PREVENTING REUSE OF MEDICAL DEVICE

(71) Applicant: Gyrus ACMI, Inc., Southborough, MA (US)

(72) Inventors: Rodney B. Loyd, Arlington, TN (US); David C. Church, Millington, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 16/431,848

(22) Filed: Jun. 5, 2019

(65) Prior Publication Data

US 2020/0078134 A1   Mar. 12, 2020

Related U.S. Application Data

(63) Continuation of application No. 16/123,888, filed on Sep. 6, 2018, now Pat. No. 10,350,025.

(51) Int. Cl.
*G08B 1/08* (2006.01)
*A61B 90/98* (2016.01)
*A61B 17/32* (2006.01)
*A61B 90/00* (2016.01)
*A61B 17/00* (2006.01)

(52) U.S. Cl.
CPC ........ *A61B 90/98* (2016.02); *A61B 17/32002* (2013.01); *A61B 90/08* (2016.02); *A61B 2017/00137* (2013.01); *A61B 2090/0803* (2016.02); *A61B 2090/0808* (2016.02); *A61B 2090/0814* (2016.02)

(58) Field of Classification Search
CPC ... A61B 90/98; A61B 90/08; A61B 17/32002; A61B 2090/0803; A61B 2090/0814; A61B 2017/00137
See application file for complete search history.

(56) References Cited

U.S. PATENT DOCUMENTS

| | | | | |
|---|---|---|---|---|
| 5,651,780 | A * | 7/1997 | Jackson | A61B 18/00 606/1 |
| 6,387,092 | B1 * | 5/2002 | Burnside | A61B 18/14 606/32 |
| 6,611,793 | B1 * | 8/2003 | Burnside | A61B 18/1206 128/897 |
| 9,833,581 | B2 * | 12/2017 | Eggert | A61M 5/20 |
| 9,943,359 | B2 * | 4/2018 | Reid, Jr. | A61B 18/1477 |
| 10,130,416 | B2 * | 11/2018 | Reid, Jr. | A61B 18/1477 |
| 2003/0023460 | A1 | 1/2003 | Ackermann et al. | |
| 2007/0129684 | A1 * | 6/2007 | Garbini | A61M 25/00 604/171 |

(Continued)

*Primary Examiner* — Phung Nguyen
(74) *Attorney, Agent, or Firm* — Harrington & Smith

(57) ABSTRACT

Provided is a medical system comprising a controller unit configured to be capable of generating a first code or coded message; and a medical device unit configured to be capable of generating a second code or coded message, the medical device unit configured to be in electronic communication with the controller unit, wherein the controller unit is configured to lock the medical device unit from being used or reused if the first code or coded message does not match or is not identical to the second code or coded message. Also provided is a method of preventing use or reuse of a medical device unit as described herein.

21 Claims, 4 Drawing Sheets

(56) References Cited

U.S. PATENT DOCUMENTS

| | | | |
|---|---|---|---|
| 2009/0065565 A1* | 3/2009 | Cao | A61B 18/1402 |
| | | | 235/375 |
| 2014/0309588 A1 | 10/2014 | Eggert et al. | |
| 2017/0311925 A1* | 11/2017 | Fokkenrood | G01S 7/5205 |
| 2018/0014872 A1* | 1/2018 | Dickerson | A61B 17/320092 |
| 2019/0008543 A1* | 1/2019 | Scoggins | A61B 17/320068 |

* cited by examiner

SYSTEM AND METHOD FOR PREVENTING REUSE OF MEDICAL DEVICE

RELATED APPLICATION

The present application is a continuation of application Ser. No. 16/123,888, filed on Sep. 6, 2018, now U.S. Pat. No. 10,350,025. The entire contents of the above application are hereby incorporated by reference.

FIELD

The present disclosure relates generally to a system and method of preventing reuse of a medical device. More particularly, the present disclosure relates to a system and method of preventing re-use of a disposable medical device such as a disposable sinus debrider or shaver by way of using a code or coded message.

BACKGROUND

U.S. Pat. No. 9,833,581 discloses a method for detecting a limit of use of a medical device including the steps of starting a timer of a medical device when the medical device is used for the first time, detecting the limit of use of the medical device and indicating the limit of use of the medical device. The limit of use is reached when at least one of a first criterion and a second criterion is met, wherein the first criterion is that the timer reaches or exceeds a time limit and wherein the second criterion is that at least one operation of a drive train of said medical device reaches or exceeds a limit.

U.S. Pat. No. 6,387,092 discloses a medical system for limiting usage of a medical probe such as a catheter and surgical probe. The disclosed medical system includes a medical probe that includes electronic storage componentry for storage of data. The disclosed medical system further includes a control unit to which the medical probe is connected. The control unit is configured for writing and reading data to and from the electronic storage componentry of the medical probe when the medical probe is connected to the control unit. The control unit includes a clock that generates a time signal, which is used to determine an initial probe usage time and a reference time. The control unit further includes a control circuit that writes the initial probe usage time to the electronic storage componentry of the medical probe when the medical probe is initially operated. During a subsequent procedure, the control circuit reads the initial probe usage time from the electronic storage componentry. The control circuit determines an elapsed probe usage time based on the initial probe usage time and the reference time. The control circuit then determines whether a predetermined elapsed time limit has expired based on the elapsed probe usage time. The control circuit then prevents operation of the medical probe if the predetermined elapsed time limit has expired.

SUMMARY

In an embodiment, the present disclosure provides a medical assembly or system. In an embodiment, the medical assembly or system comprises a controller unit. In an embodiment, the controller unit is configured to be capable of sending, receiving, processing and storing information. In an embodiment, the controller unit is configured to be capable of generating a code or coded message. In an embodiment, the controller unit is configured to be capable of receiving information requested in a query to a connected medical device unit and using this information to generate a code or coded message. In an embodiment, the query is a request or software command to the connected medical device unit to respond with a message containing identifying information and device status. In an embodiment, the controller unit is configured to be capable of transmitting the generated code or coded message to the connected medical device unit.

In an embodiment, the medical assembly or system comprises a medical device unit. In an embodiment, the medical device unit comprises a handpiece. In an embodiment, the medical device unit comprises a microprocessor. In an embodiment, the microprocessor is configured to be capable of sending, receiving, processing and storing information. In an embodiment, the microprocessor is configured to be capable of tracking, counting and storing information. In an embodiment, the microprocessor is configured to be capable of tracking, counting and storing identifying information and device status. In an embodiment, the microprocessor is configured to be capable of generating a code or coded message. In an embodiment, the microprocessor is configured to be capable of generating a code or coded message based on identifying information and device status. In an embodiment, the microprocessor is configured to be capable of comparing the generated code or coded message with another code or coded message received from outside of the medical device unit. In an embodiment, the microprocessor is housed inside the handpiece. In an embodiment, the medical device unit is independent and separate from the controller unit. In an embodiment, the medical device unit is configured to be capable of being in electronic communication with the controller unit once connected to the controller unit.

In an embodiment, the medical system comprises a device unit configured to generate a first code or coded message; and a controller unit, in electronic communication with the device unit, configured to generate a second code or coded message and to block the device unit from being used if the first code or coded message and the second code or coded message are not the same or identical. In an embodiment, the controller unit is further configured to: transmit a query to the device unit for information; receive the information from the device unit; and generate the second code or coded message according to the device unit information. In an embodiment, the query comprises a software command to request at least one of device unit identifying information and device unit status. In an embodiment, the device unit is further configured to: retrieve at least one of the device unit identifying information and the device unit status information from memory; and generate the first code or coded message according to the at least one of the device unit identifying information and the device unit status stored in its memory. In an embodiment, the device unit is configured to generate the first code or coded message as a hash value according to a hash function; and the controller unit is configured to generate the second code or coded message as the same hash value according to the same hash function. In an embodiment, the set of parameters comprises at least one of the device unit identifying information and the device unit status.

In an embodiment, the present disclosure provides a medical assembly or system comprising a controller unit and a medical device unit. In an embodiment, the present disclosure provides a medical assembly or system comprising a controller unit and a medical device unit wherein the controller unit is configured to be in control of a use or activation of the medical device unit. In an embodiment, the present disclosure provides a medical assembly or system comprising a controller unit and a medical device unit wherein the controller unit is configured to lock the medical device unit from being used, re-used or re-activated. In an embodiment, the present disclosure provides a medical assembly or system comprising a controller unit and a medical device unit wherein the controller unit is configured to unlock the medical device unit for use. In an embodiment, the present disclosure provides a medical assembly or system comprising a controller unit and a medical device unit wherein the controller unit is configured to limit a use or re-use of the medical device unit.

In an embodiment, the present disclosure provides a medical assembly or system comprising: a controller unit configured to be capable of sending, receiving, processing and storing information; and an independent medical device unit configured to be capable of being in electronic communication with the controller unit, wherein the controller unit is configured to lock the medical device unit from being used, re-used or re-activated by way of communicating a code or coded message to the medical device unit. In an embodiment, the controller unit is configured to unlock the medical device unit for use by way of communicating a code or coded message to the medical device unit.

In an embodiment, the present disclosure provides a medical system comprising: a controller unit configured to be capable of generating a first code or coded message; and a medical device unit configured to be capable of generating a second code or coded message, the medical device unit configured to be in electronic communication with the controller unit, wherein the controller unit is configured to lock the medical device unit from being used, re-used or re-activated if the first code or coded message and the second code or coded message are not the same, equal or identical. In an embodiment, the controller unit is configured to be capable of receiving information requested in a query to the medical device unit and using this information to generate the first code or coded message. In an embodiment, the query comprises a software command to request for identifying information and device status. In an embodiment, the controller unit is configured to be capable of transmitting the generated first code or coded message to the medical device unit. In an embodiment, the medical device unit is configured to generate the second code or coded message using the identifying information and the device status stored in its memory.

In an embodiment, the present disclosure provides a method of locking a medical device unit from being used or re-used, the method comprising: providing the medical device unit; providing a separate controller unit, and connecting the controller unit and the medical device unit, wherein the controller unit is configured to lock the medical device unit from being used or re-used by way of communicating a code or coded message to the medical device unit based on processing an input it receives from the medical device unit.

In an embodiment, the present disclosure provides a method of locking a medical device unit from being used or re-used, the method comprising: providing the medical device unit having a microprocessor capable of sending, processing, and storing information; providing a separate controller unit configured to be capable of receiving, processing an input from the medical device unit, and connecting the controller unit and the medical device unit; wherein the controller unit locks the medical device unit from being used or re-used by way of communicating a code or coded message to the medical device unit based on processing the input it receives from the medical device unit.

In an embodiment, the present disclosure provides a method of unlocking a medical device unit for use, the method comprising: providing the medical device unit; providing a separate controller unit, and connecting the controller unit and the medical device unit, wherein the controller unit unlocks the medical device unit for use by way of communicating a code or coded message to the medical device unit based on processing an input it receives from the medical device unit.

In an embodiment, the present disclosure provides a method of unlocking a medical device unit for use, the method comprising: providing the medical device unit having a microprocessor capable of sending, processing, and storing information; providing a separate controller unit configured to be capable of receiving and processing an input from the medical device unit, and connecting the controller unit and the medical device unit; wherein the controller unit unlocks the medical device unit for use by way of communicating a code or coded message to the medical device unit based on processing the input it receives from the medical device unit.

In an embodiment, the present disclosure provides a method of limiting a use or re-use of a medical device unit, the method comprising: providing the medical device unit having a handpiece configured to be equipped with a microprocessor capable of tracking, counting, and storing a set of parameters; providing a separate controller unit configured to be capable of receiving and processing an input from the medical device unit, connecting the medical device unit and the controller unit, and generating a code or coded message, wherein the controller unit limits the use or re-use of the medical device unit if the code or coded message does not meet an established criterion or condition.

In an embodiment, the present disclosure provides a method of limiting a use or re-use of a medical device unit, the method comprising: providing the medical device unit having a handpiece configured to be equipped with a microprocessor capable of sending, processing, and storing a set of parameters; providing a separate controller unit configured to be capable of receiving, processing, and storing an input from the medical device unit, and connecting the medical device unit and the controller unit, wherein the controller unit limits the use or re-use of the medical device by way of communicating a code or coded message to the microprocessor of the medical device unit when the code or coded message does not meet an established criterion or condition.

In an embodiment, the present disclosure provides a method of blocking a use or re-use of a medical device unit, the method comprising: providing a controller unit configured to be capable of generating a first code or coded message; providing the medical device unit having a handpiece configured to be equipped with a microprocessor capable of generating a second code or coded message; and connecting the medical device unit with the controller unit, wherein the controller unit blocks the use or re-use of the medical device when the first code or coded message does not match the second code or coded message.

DETAILED DESCRIPTION

Figure 1:
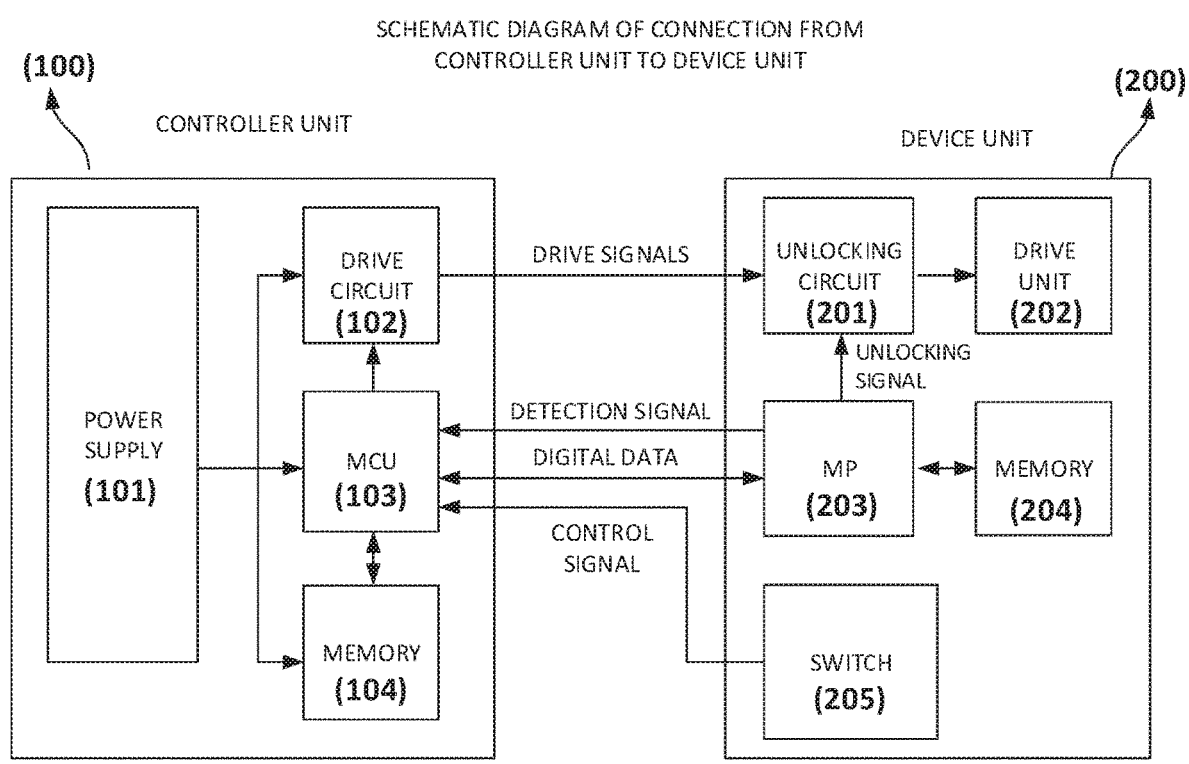
FIG. 1 is a block diagram illustrating a system according to an example embodiment of the present disclosure.

FIG. 1 is a block diagram illustrating a system 10 according to an example embodiment of the present disclosure. The system 10 includes a controller unit 100 and a device unit 200 which electronically interact. In certain embodiments, the device unit 200 may be a medical device. It should be understood that the block diagram may be similarly used or adapted for the interactions of the controller unit of the medical system with the other components as described herein or known in the art. The system 10 may also include other components or accessories such as a control panel, an irrigation related assembly, a suction related assembly, a power supply related assembly, and a cutting member related assembly.

As illustrated in FIG. 1, the controller unit 100 of the medical system 10 comprises a power supply 101, a drive circuit 102 (e.g., a solenoid driver), and a microcontroller or microcontroller unit (MCU) 103. It should be understood that more components or electric circuits may be possible or desirable in order to accommodate different operational needs. The device unit 200 comprises a switch 205, a microprocessor (MP) 203, memory 204, an unlocking circuit 201, and a drive unit 202 (e.g., a solenoid). The device unit 200 is configured to be capable of being in electronic communication with the controller unit 100, and the electronic communication may be through a signal from the switch 205, such as a push button or knob.

The controller unit 100 may be configured to receive an input from the switch 205 located on the device unit 200 to generate an output to control the operation of the device unit's working element/member such as a cutting blade (not shown). The control signal may also come from a foot press of a footswitch to generate an output to control the motion of the medical device's working element. In the above embodiments, the controller unit 100 is also configured to monitor and detect times that the device unit 200 is connected.

It should be understood that the device unit 200 may also be configured to have other types of control modes such as voice control. Additional communication with the controller 100 unit may be through a digital serial data signal or through discrete signals containing analog or digital information.

The MCU 103 of the controller unit 100 may be a microprocessor, an application specific integrated circuit (ASIC) state machine, a gate array, and the like so long as it can perform the desired functions and activities as described herein. More particularly, the MCU 103 may receive inputs from the power supply 101, switches, and similar components of the system 10. In certain embodiments, basic components of the MCU 103 may include input modules, a central processing unit, output modules, and a programming device. The MCU 103 may comprise more than one such unit as needed. The MCU 103 is configured to monitor the system 10 status (e.g., to detect times that a device unit 200 is connected), to process user inputs (e.g., from the switch 205), and to generate control signals to control the drive circuit 102. The controller unit 100 may include a display (not shown) and user input device (not shown) which may allow a user to input parameters or values.

The drive circuit 102 is configured to deliver a drive signal to the device unit 200. The drive circuit 102 may be a MOSFET drive circuit. In certain embodiments the drive circuit 102 may be a solenoid driver and the drive unit 202 may be a solenoid, with the drive circuit 102 configured to send drive signals to the solenoid 202. It should be understood that other drivers may be similarly used to send drive signals to a variety of devices with different driving mechanisms. For example, the drive unit 202 may be a motor unit which may comprise a linear motion device such as a solenoid, or a rotational motion device such as a rotating motor.

The device unit 200 may be configured to comprise a microprocessor (MP) 203. The MP 203 is configured to monitor the system 10 status, to process user inputs (not shown), and to perform other functions in connection with the device unit 200. For example, the MP 203 is configured to electronically control the unlocking circuit 201 based on instructions from the controller unit 100. The unlocking circuit 201 may receive a signal from the microprocessor 203 to control the activation of the unlocking circuit 201.

The microprocessor 203 is configured to be capable of sending, receiving, processing, tracking, counting, and storing information about the device unit 200, such as a unique and serialized device ID number and device status based on certain operational parameters or operation history. The device unit 200 ID number may be stored at the time of device unit manufacture. Other information that may be stored includes device unit 200 status based on certain operational parameters or operation history, both of which may be stored, updated or modified by the microprocessor 203 during the operation of the device unit 200. The information regarding the device unit 200 may be stored in internal memory of the microprocessor 203 or in an external memory unit 204.

The unlocking circuit 201 may be a MOSFET switch, MOSFET drive circuit, a solid state relay or other electronically controlled unlocking mechanism which functions to either allow or prevent passage of the power signals or drive signals to the drive unit 202 in order to allow or prevent drive unit 202 operation based on the instructions such as drive signals from the drive circuit 102 of the controller unit 100. In certain embodiments, the drive unit 202 may be a solenoid or other electro-mechanical driving mechanism to deliver a driving force to a working element such as a cutting blade, burr or bit (not shown).

FIG. 1 also illustrates interactions between the controller unit 100 and the device unit 200. Communications from the controller unit 100 with a connected device unit 200 can include sending a query to determine whether a device unit 200 is connected. In certain embodiments, the query is a request or software command to the device unit 200 to respond with a message containing, for example, device unit 200 identifying information and device status information. The identifying information can be information such as a unique and serialized device ID number such that no other connected device (either the same or a different model of the connected device) can have the same device ID number. Device status can be information that defines certain operational parameters or operation history based on information that is tracked, counted or stored in the connected device, such as usage status (i.e. used or unused), a count of the number of times the device was power up (i.e. power cycle count) or other parameters. Other parameters could include, but are not limited to the time operated, the time powered up, the number of activations of an activation switch, or the number of cycles, rotations, strokes or reciprocations of a motor, of a connected device.

The MCU 103 is configured to receive and store the message in memory 104 that is returned from the query command sent to the device unit 200. The MCU 103 is also configured to process the message received from the query command by, for example, analyzing the usage status of the device unit 200 to determine if the device unit 200 has been used previously, and then accordingly whether the device unit 200 should be locked or unlocked.

The microprocessor 203 of the device unit 200 is also configured to respond to queries from the controller unit 100 by transmitting information about the device unit 200 such as a unique or serialized device unit ID number and device unit status based on certain operational parameters or operation history. The microprocessor 203 of the device unit 200 is also configured to receive and process information from the controller unit 100 such as a code or coded message that was generated by the controller unit 100 using information originally sent to the controller unit 100 by the microprocessor 203 of the device unit 200 in response to a query from the controller unit 100.

The microprocessor 203 is configured to be capable of generating a code or coded message. The code or coded message can be based on certain information that is tracked, counted or stored such as a unique and serialized device unit ID number and device unit status. The code or coded message generated by the microprocessor 203 may be in the form of a hash value generated from a hash function. The hash function may be a specific hash function that is programmed into the embedded software program being executed by the microprocessor 203. The specific hash function used to generate the code or coded message is the same specific hash function used by the controller unit 100 to generate its code or coded message.

The microprocessor 203 is configured to be capable of comparing a code or coded message that is generated to another code or coded message that is received from the controller unit 100 to determine if the generated and received codes or coded messages are equal. The microprocessor 203 is configured to be capable of using the results of the comparison to generate a signal that can be used to control the unlocking circuit 201. In certain embodiments, the unlocking circuit 201 may be a locking or unlocking mechanism or circuit which may comprise an electronically controllable component that has the capability to prevent or allow the transmission of power or drive signals to the motor unit in a way that prevents operation of the drive unit 202. By sending the signal to the unlocking circuit 201 in response to the comparison of the generated code or coded message with the received code or coded message, the microprocessor 203 is able to prevent the reuse of the device unit 200 because the drive signals cannot pass to the drive unit without unlocking the unlocking circuit by the microprocessor 203. It should be understood that the controller unit only needs to know whether the device unit is new or used which it can read from the device unit's memory through the query command. It should also be understood that the usage status of each device unit is carried along with it, and consequently each controller unit will make the same determination when a device unit is plugged into the system.

In certain embodiments, the MCU 103 may consider the device unit 200 as being used if it has been connected to the controller unit 100 only once or more than once. More particularly, a device unit carries in its memory a count of how many times it has been connected to a controller unit, and the device unit's use status may then be based on this information. For example, when a device unit is plugged in first time to be for testing at the factory, it does not get updated to "used" even though it has been plugged in once. It will be updated to "used" at a second time when it is plugged in by a user. In other embodiments, the MCU 103 may consider the device unit 200 as being used based on the elapsed time for which it has been connected to the controller unit 100 or based on an elapsed time of operation of the device unit 200. In yet other embodiments, the MCU 103 may consider the device unit 200 as being used based on a number of activations of the device unit 200 (e.g., such as by an activation switch 205), a number of times the device unit 200 has been powered up or powered down, or a number of cycles, rotations, or reciprocations of the motor or other mechanical component of the device unit 200. It should be understood that the controller unit does not necessarily keep a record for each device unit after the device unit has been unplugged. It may store the information in the device unit's memory. It may also just start at zero at the time when the device unit is plugged in and tabulate the values as it is in operation. Further, the MCU 103 may consider the device unit 200 as being used based on any combination of the above factors.

Because the MCU 103 is configured to receive and store the message returned from the query command containing identifying information and device status, the MCU 103 is able to identify when a device unit 200 has been unplugged and reconnected by comparing the received identifying information and the device status to stored identifying information and device status.

When a device unit 200 has been detected that has been temporarily unplugged and then reconnected to the controller unit 100, the MCU may allow for a grace period of time for the device unit 200 such that, if the device unit 200 was unplugged and then reconnected to the controller unit 100 within the time limits of the grace period, the controller unit 100 may allow the device unit 200 to be enabled even though the processing of the device status by the MCU 103 indicates that the device unit 200 is used. The grace period may also be evaluated in combination with the other parameters that are used to evaluate whether the device unit 200 is considered as being used in order to determine whether or not the operation under the grace period should be allowed and that the device unit 200 should be enabled. By evaluating whether the device unit 200 is new or used, or whether a used device unit 200 should be allowed to operate under a grace period, the MCU 103 is configured to generate a code or coded message that is capable of locking or unlocking the medical device unit and then transmitting the code or coded message to the medical device unit. The code or coded message generated by the MCU may be in the form of a hash value generated from a hash function. The hash function may be a specific hash function that is programmed into the embedded software program being executed by the MCU.

In example embodiments, the controller unit 100 and the device unit 200 are both configured to generate a code or coded message. The code or coded message may be in the form of a hash value from a hash function. The hash function is used to encode an input data string called a "message", and generate an output string called a "hash value". Ideally, a hash function should have the following five main properties: the same message always results in the same hash value; a processor can quickly compute a hash value for any given message; it is infeasible to generate a message from its hash value except by trying all possible messages; a small change to a message results in a change to the hash value so extensive that the new hash value appears uncorrelated with the old hash value; and two different messages do not result in the same hash value. It should be understood that the hash value is essentially a secure code for the message, and can be used as means for two devices to authenticate each other by comparing the generated hash values for the same input message. Only devices that are programmed with the same hash function would be able to generate the correct hash value from a given message. Moreover, it is nearly impossible to reverse engineer a unique hash function from a given message and hash value. Therefore, in the embodiments described in the present disclosure, the hash function executed by the embedded software program running on the controller unit's MCU and the hash function executed by the embedded software running on the medical device unit's microprocessor must be identical, and must generate the same hash value for any given input to the hash function.

More particularly or more preferably, the present disclosure uses a binary combination of a set of parameters such the device ID, power cycle count, and usage status as the source of the input message to the hash function to generate a hash value. It should be understood that other or more parameters may be used as the input message to the hash function to generate the hash value to further increase the security or complexity of the hash value. As an example, a 4-bit device ID and 4-bit power cycle count may be used to construct an 8-bit message, which is then used as the input for the hash function. Of course, a 16-bit, 32-bit or even more message may also be created for use as the input to the hash function. As for the code or coded message or hash value, a 32-bit, 64-bit, or even more bits may be used although typically the hash value bit length is selected to be larger than the bit length of the input message. The more bits used in the hash value, the more secure it is. The use of values that change from unit-to-unit such as device ID and values that change each time the handpiece is connected such as the power cycle count results in a constantly changing input message that is unique for each unit that is produced, and is different each time the unit is powered on. Consequently, the hash value is impractical to predict, guess, or reverse-engineer. This results in a very secure scheme for limiting the use of a one-time use medical device.

In the above embodiments, both the controller unit 100 and the device unit 200 may be configured to generate unique codes or coded messages in the form of hash values in accordance with the needs and/or requirements of a manufacturer of the device unit 200 and the controller unit 100. It should be understood that the MCU 103 of the controller unit 100 and the microprocessor 203 of the device unit 200 manufactured as such should also be able to carry out those functions in a manner as described above.

In the above embodiments, the controller unit 100 may be configured to be housed in a power pack as disclosed in U.S. patent application Ser. No. 16/016,796 filed on Jun. 25, 2018, the whole contents of which are fully incorporated herein for reference. The controller unit 100 may also be disposed inside a control panel. The controller unit 100 may also be an independent unit that is portable or disposable.

In the above embodiments, the device unit 200 may be a debrider or shaver such as a disposable tonsil adenoid debrider (DTAD) from Olympus Corporation. The device unit 200 may be a microdebrider or a sinus debrider, or a shaver, which may be disposable. It may be any other suitable medical devices such as disclosed in the U.S. Pat. Nos. 7,226,459, 7,510,563, and 7,666,200, the entire contents of which are all incorporated herein for reference.

It should be understood that the controller unit 100 can detect a connection of the controller unit 100 with the device unit 200 once the device unit 200 is connected to the controller unit 100. It should also be understood that the controller unit 100 communicates with the device unit 200 through the MCU 103 of the controller unit 100 and the microprocessor 203 of the device unit 200 at times the two are connected. Data is transmitted between the controller unit 100 and the device unit 200. Electronic communications/transmissions will be explained in more detail in FIG. 2, FIG. 3, and FIG. 4, respectively.

It should be understood that the device unit 200 will be activated only after the controller unit 100 confirms the device unit 200 possesses the required parameters for activation and allows unlocking of the device unit 200 via a signal to the MP203 to unlock the unlocking circuit 201. It should be understood these communications and/or transmissions may be performed in the background in a manner that does not produce a noticeable delay to the user that is using the device unit 200 in the normal manner. Following the connection, if a user pushes or activates the switch 205 of the device unit 200, the controller unit MCU 103 will then instruct the drive circuit 102 to send drive signals toward the drive unit 202 in the device unit 200 which will pass through the unlocking circuit 201 which has been activated by the device unit microprocessor 203 after the device unit 200 has received a valid unlocking code from the controller unit. It should be understood that the device unit 200 will not be activated for operation if it does not receive a matching unlocking code from the controller unit 100 which will be determined upon the controller unit's evaluation of the device unit 200.

Figure 2:
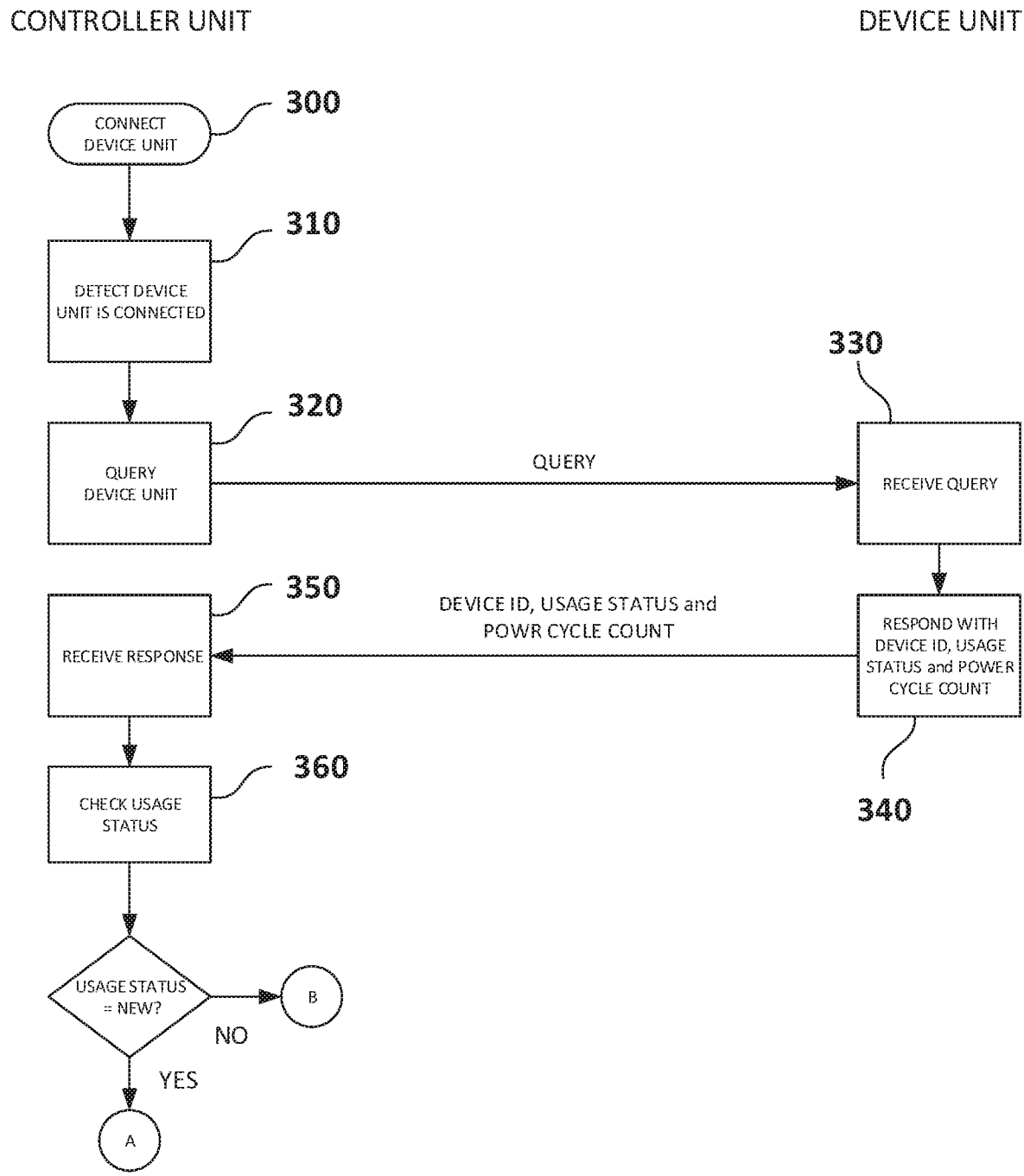
FIG. 2 is a flow diagram illustrating a first connection of a medical device unit with a controller unit in accordance with one aspect of the present disclosure.
Figure 3:
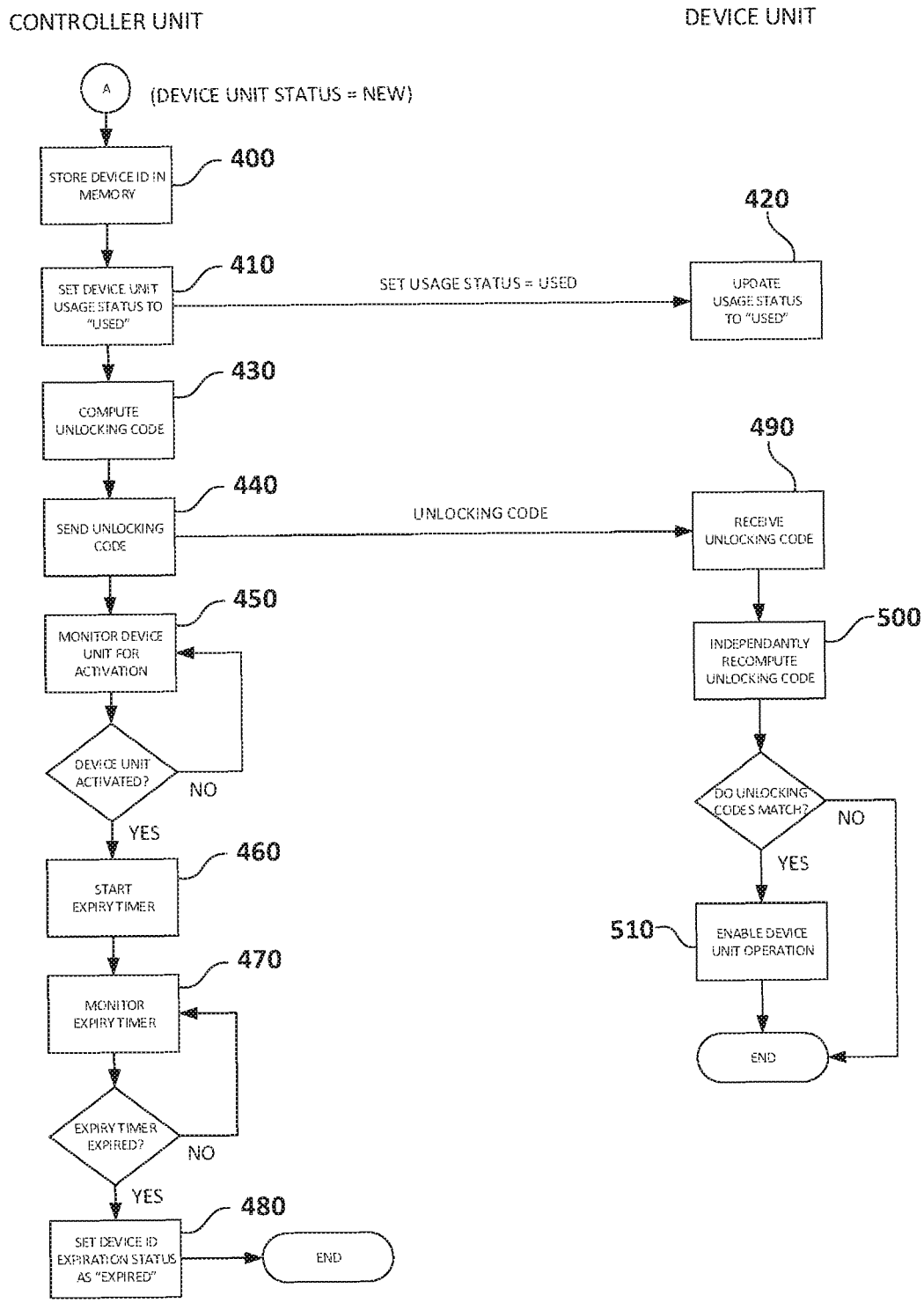
FIG. 3 is a flow diagram illustrating a first use of a medical device unit with a controller unit in accordance with a situation as shown in FIG. 2.
Figure 4:
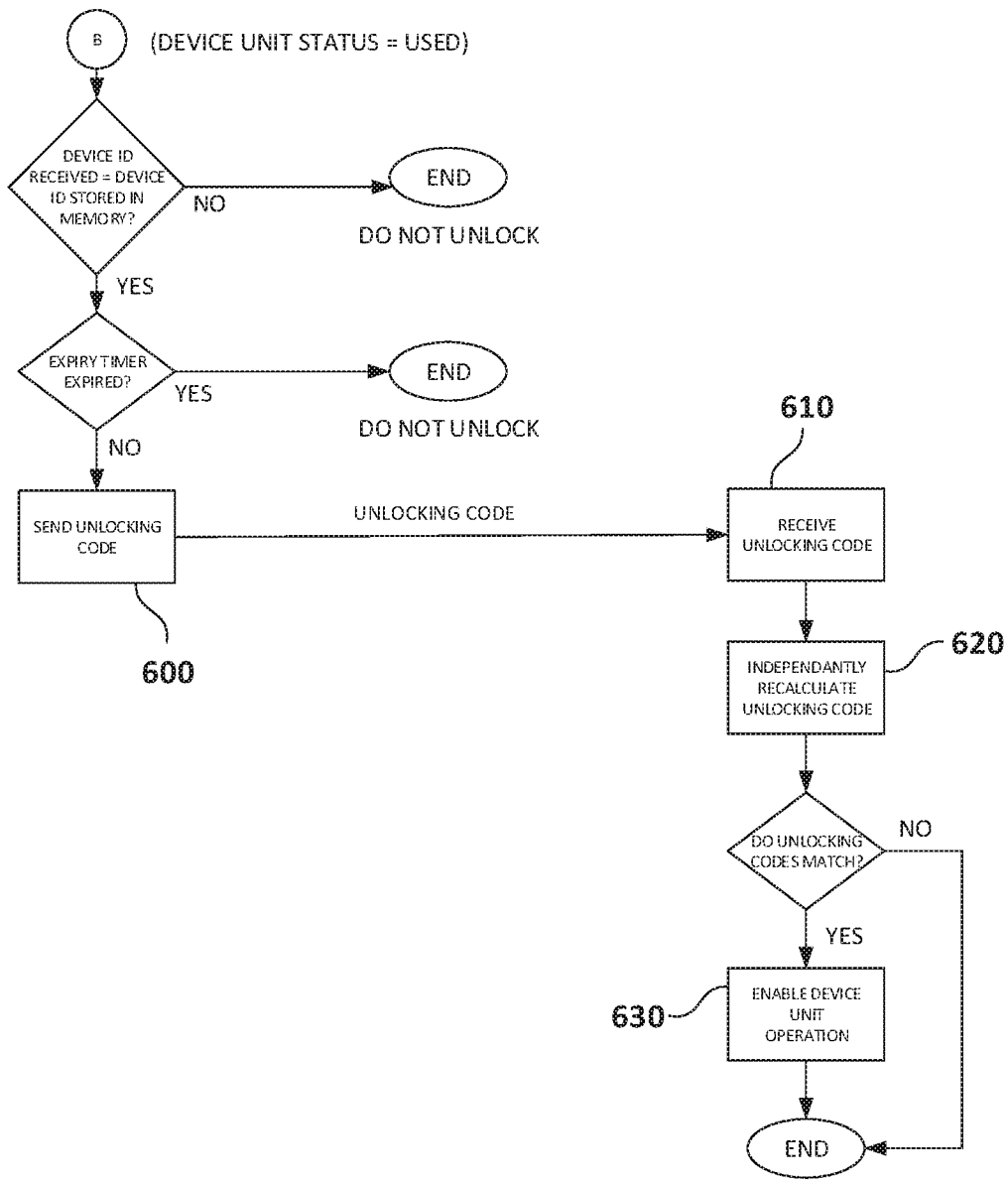
FIG. 4 is a flow diagram illustrating a used situation of a medical device unit with a controller unit in accordance with a situation as shown in FIG. 2.

FIG. 2 is a flow diagram illustrating communications of a controller unit (such as the controller unit 100 of FIG. 1) with a device unit (such as the device unit 200 of FIG. 1) at times the device unit is connected to the controller unit in accordance with one aspect of the present disclosure (step 300). It should be understood that the controller unit is configured to be capable of detecting a connection once a device unit is connected to it (step 310), and it will then send a query to the device unit for information (step 320). After receiving the query (step 330), the device unit is configured to send a response with the requested information such as the device ID, the usage status and the power cycle count (step 340). It should be understood the device ID, the usage status and the power cycle count may all be coded in binary codes. After receiving the response or the requested information from the device unit (step 350), the controller unit checks the status of the device unit usage based on the received information (step 360), and follows the procedure A as shown in FIG. 3 if the status check indicates the device unit is new or first time connection or otherwise is not considered used. Otherwise, the controller unit performs the procedure B as shown in FIG. 4 if the status check indicates the device unit is not new or not first time connection or otherwise is considered used.

As discussed with respect to FIG. 2, the controller unit will follow the procedure A when it detects that a connected device unit is new or first time connection or otherwise is not considered used. FIG. 3 is a flow diagram illustrating interaction between the controller unit and the device unit at times the controller unit detects the device unit is new or first time connection or otherwise is not considered used. It should be understood that the controller unit generally only looks to see if the device unit is new or used. If it identifies the device unit as new, then it will allow it to operate as new. If it identifies as used, it will then check to see if the device ID is stored in the memory, and check whether it is expired or not. The controller unit will only allow operation if it is stored in the memory and it is not expired. It should be understood that the controller unit may be configured to store only one device ID in its memory at one time. When a new device unit is plugged in, the controller unit overwrites the previous device ID that was stored. It should also be understood that the controller unit does not need to know whether a device unit has been previously plugged to a different controller unit. As stated above, it only needs to know whether the device unit is new or used. It should be further understood a "used" device unit may only be operated on the controller unit that it was originally plugged in to because the controller unit only stores the device ID in the memory when the device unit is new (referring to FIG. 3). The process for evaluating each device unit should be the same regardless of which controller unit it is connected to, or whether it has been connected before. It should also be understood that in the case when it was plugged into another controller unit but not long enough to be marked as "used", it will still operate as a "new" device unit on any controller unit it is connected to. Once confirmed as a first time connection, the controller unit will store the device ID in its memory (step 400), and it will subsequently set the device unit status as used (step 410) and communicates this information to the device unit so that the use status will accordingly be updated as used in the memory of the device unit (step 420). The controller unit will compute a code or a hash value (also known as an unlocking code) based on a set of pre-defined parameters through a pre-defined hash function (step 430), and communicate or transmit the code or the hash value to the device unit (step 440). The device unit receives the transmitted code or coded message (step 490), and it also independently recalculates its own code or hash value through its own microprocessor based on the set of parameters it has in its memory (step 500). If the recalculated code or hash value from the device unit matches the code or hash value from the controller unit, the device unit's microprocessor will unlock or enable the device unit for operation by sending a control signal to the unlocking circuit or mechanism in the device unit (step 510). If the controller transmits a code or hash value that does not match the device unit's calculated code or hash value (i.e. an invalid unlocking code), the device unit microprocessor will not enable the device unit for operation.

Additionally, after sending the device unit a valid or matching unlocking code to enable device unit operation, the controller unit will closely monitor the activation status of the device unit by monitoring the pushbutton or activation switch (step 450). After the controller unit detects that the device unit has been activated, the controller unit will start an expiry timer which is used to control the allowable time period that the device unit may be used after starting of the timer (step 460). This is primarily to account for the possibility that the device unit may be accidentally disconnected from the controller unit during use and then subsequently reconnected, but it may also be used to limit the actual usage time of the device unit. A defined time period that the device unit can be disconnected from the controller unit and then reconnected, such that operation is still allowed can be referred to as a grace period. The controller unit may also be configured so that the expiry timer will not be started unless the device unit is actually activated for operation. It should be understood that the device unit activation means that the push button of the device unit is intentionally pushed or activated. In order to prevent accidental activation or pushing of the push button, the activation time may be set at a value, for example, 2, 4, 6 seconds, or even longer. Other criteria may also be used to establish that the device unit has been intentionally activated. The controller unit will start the expiry timer only if it detects that the device unit is activated. It is expected that the controller unit will closely monitor the expiry timer so that the device unit can only be used within a certain time limit to safeguard the safety of using the device unit (step 470). The expiry timer may be pre-defined at a reasonable number such as 30 minutes, 1 hour, 2 hours, or even up to 6 hours depending on the nature of the device unit. If the expiry timer has expired, the controller unit will set the ID expiration status as expired (step 480) and the device unit will no longer be capable of being enabled. It should be understood that the timing applied to the expiry timer will be pre-determined and programmed into the embedded software running on the Controller Unit's MCU. It should also be understood that the device unit may be connected or disconnected several times. However, if it is reconnected again even if it's within a short period of time, it will then follow a procedure as shown in FIG. 4. If it is still first connected, but for a time period longer than the pre-defined expiry time, the controller unit may also block or lock the device unit from being used further, and an operator will have to select another device unit for use.

As discussed with respect to FIG. 2, the controller unit will follow the procedure B when it detects the connected device unit status as used. FIG. 4 is a flow diagram illustrating interaction between the controller unit and the device unit at times the controller unit detects the device unit is used. As illustrated in FIG. 2, after the device unit has been connected to the controller unit, and the controller unit detects the connection and issues a query to the device unit, and then receives the device ID and device status that is set to "used". As illustrated in FIG. 3, the controller unit will then check whether or not the device ID number of the used device unit is the same as one stored in the controller unit's memory. If the device ID numbers match, this indicates that this particular device unit was previously connected to the controller unit. If the device ID numbers do not match, the controller unit will not send a valid unlocking code to the device unit to enable operation. The controller is thus configured to prevent any unauthorized device unit from being used. The controller unit will go to next step to check whether or not the expiry timer has expired if it finds a match with the stored ID number. Again, the controller unit will not unlock the device unit for use if the expiry timer is found to be expired. It will communicate a code or coded message to the device unit if it finds the expiry timer has not expired, which is the unlocking code for device unit (step 600). It should be understood that the expiry timer may accumulatively be set at any reasonable number such as 30 minutes, 1 hour, 2 hours, or even up to 6 hours depending on the nature of the medical device unit. The device unit receives the transmitted code or coded message (step 610), and it also independently recalculates its own code or hash value through its own microprocessor based on the set of parameters it has in its memory (step 620). If the recalculated code or hash value from the device unit matches the code or hash value from the controller unit, the device unit's microprocessor will unlock or enable the device unit for operation by sending a control signal to the unlocking circuit or mechanism in the device unit (step 630). If the controller transmits a code or hash value that does not match the device unit's calculated code or hash value (i.e. an invalid unlocking code), the device unit microprocessor will not enable the device unit for operation.

In an embodiment, the present disclosure provides a method comprising: identifying a device unit; determining a use state of the device unit; and controlling operation of the device unit according to the determination. In an embodiment, identifying a device unit comprises: querying the device unit for information identifying the device unit; and receiving information identifying the device unit. In an embodiment, receiving information identifying the device unit comprises receiving device unit use state information; and determining a use state of the device unit comprises determining whether the use state information for the device unit indicates that the device unit has been used or whether the use state information for the device unit indicates that the device unit has not been used. In an embodiment, the method further comprising, if the use state information for the device unit indicates that the device unit has been used: determining whether the information identifying the device unit is equal to a previous information identifying a last identified device unit; and determining, if the information identifying the device unit is equal to the previous information identifying the last identified device unit, whether a period of time associated with the present identification exceeds a threshold. In an embodiment, the period of time is determined according to a time of the present identification and a time of the previous identification.

In an embodiment, the present disclosure provides a method of locking a device unit from use or reuse. In an embodiment, the method includes providing a medical device unit. The medical device unit may be configured to have a handpiece with a microprocessor disposed inside the handpiece. In an embodiment, the microprocessor is configured to be capable of sending, receiving, processing and storing information. In an embodiment, the microprocessor is configured to be capable of tracking, counting and storing information. In an embodiment, the microprocessor is configured to be capable of tracking, counting and storing identifying information and device status. In an embodiment, the microprocessor is configured to be capable of generating a code or coded message. In an embodiment, the microprocessor is configured to be capable of generating a code or coded message based on identifying information and device status. In an embodiment, the microprocessor is configured to be capable of comparing the generated code or coded message with another code or coded message received from outside of the medical device unit. In an embodiment, the method includes providing a controller unit configured to be capable of receiving, sending, processing, and storing information. In an embodiment, the method includes providing a controller unit configured to be capable of generating a code or coded message. In an embodiment, then method includes providing a controller unit configured to be capable of receiving information requested in a query to a connected device and using this information to generate a code or coded message. In an embodiment, then method includes providing a controller unit configured to be capable of transmitting a generated code or coded message to a connected device. The controller unit is configured to be in electronic communication with the medical device unit. In an embodiment, the method includes connecting the medical device unit with the controller unit. In an embodiment, the method includes communicating a code or coded message from the controller unit to the medical device unit to lock the medical device unit from being used or reused if the code or the message does not match a code or coded message generated by the medical device unit. In an embodiment, the method includes disposing of the medical device unit if it is found to be previously used or activated longer than a pre-defined time.

In an embodiment, the present disclosure provides a method of limiting a use of a medical device unit. In an embodiment, the method includes providing a medical device unit. The medical device unit may be configured to have a handpiece with a microprocessor disposed inside the handpiece. In an embodiment, the method includes providing a controller unit configured to be capable of receiving, sending, processing, and storing information. In an embodiment, the controller unit may be capable of generating a code or coded message. In an embodiment, the controller unit is configured to be capable of receiving information requested in a query to a connected medical device unit and using this information to generate a code or coded message. In an embodiment, the query is a request or software command to the connected medical device unit to respond with a message containing identifying information and device status. In an embodiment, the controller unit is configured to be capable of transmitting the generated code or coded message to the connected medical device unit. The controller unit is configured to be in electronic communication with the medical device unit. In an embodiment, the method includes connecting the medical device unit with the controller unit. In an embodiment, the method includes communicating the code or coded message from the controller unit to the medical device unit to limit the use of the medical device unit if the code or coded message does not satisfy an established criterion.

In an embodiment, the present disclosure provides a method of unlocking a medical device unit for use. In an embodiment, the method includes providing a medical device unit. The medical device unit may be configured to have a handpiece with a microprocessor disposed inside the handpiece. In an embodiment, the method includes providing a controller unit configured to be capable of receiving, sending, processing, and storing information. In an embodiment, the controller unit may be capable of generating a code or coded message. In an embodiment, the controller unit is configured to be capable of receiving information requested in a query to a connected medical device unit and using this information to generate a code or coded message. In an embodiment, the query is a request or software command to the connected medical device unit to respond with a message containing identifying information and device status. In an embodiment, the controller unit is configured to be capable of transmitting the generated code or coded message to the connected medical device unit. The controller unit is configured to be in electronic communication with the medical device unit. In an embodiment, the method includes connecting the medical device unit with the controller unit. In an embodiment, the method includes communicating the code or coded message from the controller unit to the medical device unit to unlock the medical device unit for use if the code or coded message meets an established criterion.

In an embodiment, the present disclosure provides a method of locking a medical device unit from being used or re-used, the method comprising: providing the medical device unit; providing a separate controller unit, and connecting the controller unit and the medical device unit, wherein the controller unit is configured to lock the medical device unit from being used or re-used by way of communicating a code or coded message to the medical device unit based on processing an input it receives from the medical device unit.

In an embodiment, the present disclosure provides a method of locking a medical device unit from being used or re-used, the method comprising: providing the medical device unit having a microprocessor capable of storing information; providing a separate controller unit configured to be capable of receiving and processing an input from the medical device unit, and connecting the controller unit and the medical device unit; wherein the controller unit locks the medical device unit from being used or re-used by way of communicating a code or coded message to the medical device unit based on processing the input it receives from the medical device unit.

In an embodiment, the present disclosure provides a method of unlocking a medical device unit for use, the method comprising: providing the medical device unit; providing a separate controller unit, and connecting the controller unit and the medical device unit, wherein the controller unit unlocks the medical device unit for use by way of communicating a code or coded message to the medical device unit based on processing an input it receives from the medical device unit.

In an embodiment, the present disclosure provides a method of unlocking a medical device unit for use, the method comprising: providing the medical device unit having a microprocessor capable of receiving, processing, sending and storing information; providing a separate controller unit configured to be capable of receiving and processing an input from the medical device unit, and connecting the controller unit and the medical device unit; wherein the controller unit unlocks the medical device unit for use by way of communicating a code or coded message to the medical device unit based on processing the input it receives from the medical device unit.

In an embodiment, the present disclosure provides a method of limiting a use of a medical device unit, the method comprising: providing the medical device unit having a handpiece configured to be equipped with a microprocessor capable of receiving, processing, sending and storing a set of parameters; providing a separate controller unit configured to be capable of receiving and processing an input from the medical device unit, connecting the medical device unit with the controller unit, and generating a code or coded message, wherein the use of the medical device unit is limited if the code or coded message does not meet an established criterion.

In an embodiment, the present disclosure provides a method of limiting a use of a medical device unit, the method comprising: providing the medical device unit having a handpiece configured to be equipped with a microprocessor capable of receiving, processing, sending and storing a set of parameters; providing a separate controller unit configured to be capable of generating and transmitting a hash value based on an input from the medical device unit, and connecting the medical device unit with the controller unit, wherein the use of the medical device is limited if the hash value the medical device unit receives does not meet an established criterion.

In an embodiment, the present disclosure provides a method of limiting use of a medical device unit, the method comprising: providing the medical device unit having a handpiece configured to be equipped with a microprocessor capable of receiving, processing, sending and storing a set of parameters; providing a separate controller unit configured to be capable of generating a code or coded message based on the set of the parameters it receives from the medical device unit; and communicating or transmitting the code or coded message to the microprocessor of the medical device unit, wherein the use of the medical device unit is limited if the code or coded message does not meet or match an established criterion.

In an embodiment, the present disclosure provides a method of blocking use of a medical device unit, the method comprising: providing a controller unit configured to be capable of generating a first hash value from a set of parameters; providing the medical device unit configured to be capable of independently generating a second hash value from the set of parameters, the medical device unit configured to be capable of being in electronic communication with the controller unit; connecting the controller unit with the medical device unit; and communicating the first hash value to the medical device unit, wherein the medical device unit is blocked from use if the first hash value does not match or is not identical to the second hash value. In an embodiment, the set of parameters may be a medical device unit unique identification (ID) number, the usage status and/or the power cycle count. In an embodiment, the set of parameters may be in binary codes. In an embodiment, the hash value is generated by a hash function. In an embodiment, the set of parameters are used for the hash function to generate a hash value.

In an embodiment, the present disclosure provides a method of blocking use of a medical device unit, the method comprising: providing the medical device unit; providing a controller unit; connecting the controller unit with the medical device unit; generating, by the controller unit, a first hash value from a set of parameters; and generating, by the medical device unit, a second hash value from the set of parameters, wherein the controller unit is configured to block the medical device unit from being used if the first hash value does not match or is not identical to the second hash value.

In the above embodiments, the method may comprise providing a controller unit wherein the controller unit is configured to be equipped with one or more of a microcontroller or MCU capable of sending, receiving, processing, and storing information and wherein the controller unit is configured to be capable of being electronic communication with all the components that may be necessary for the medical system as described herein. In the above embodiments, the controller unit may be capable of generating a hash value from a hash function. In an embodiment, the controller unit may be capable of transmitting the generated hash value to a connected medical device unit. In the above embodiments, the method may comprise providing a medical device unit wherein the medical device unit is configured to comprise a microprocessor capable of sending, receiving, processing, and storing information, memory unit, an unlocking circuit, power switch or unlocking mechanism, a driving unit, and a push button wherein the medical device unit is configured to be in electronic communication with the controller unit once connected. In the above embodiments, the medical device unit may be capable of generating a hash value from a hash function. In the above embodiments, the medical device unit may be capable of comparing the generated hash value with a hash value received from outside of the medical device unit.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The principles of the present disclosure may be better understood with reference to the drawings and the accompanying descriptions, wherein like reference numerals have been used throughout to designate identical or similar elements. It should be understood that these drawings are not necessarily are drawn to scale. They are presented just for illustrative purposes only, and are not intended to limit the scope of the disclosure. Examples of materials, dimensions, and constructions are included for some elements. Those of ordinary skill in the art should understand that many of the examples provided have suitable alternatives and these alternatives should also be considered within the scope of this disclosure. Moreover, certain terminology is used herein for convenience only and is not to be taken as a limitation on the present disclosure.

The explanations and illustrations presented herein are intended to acquaint others skilled in the art with the disclosure, its principles, and its practical applications. Those skilled in the art may adapt and apply the disclosure in numerous forms, as may be best suited to the requirements of a particular use. The specific embodiments of the present disclosure as set forth are not intended to be exhaustive or limiting of the invention. The scope of the invention should be determined not with reference to the above description, but should be determined with reference to the appended claims, along with the full scope of equivalents to which such claims are entitled.

The terms "one embodiment", "an embodiment", "another embodiment", "some embodiments", "other embodiments", "above embodiment", and similar expressions indicate that the embodiment or embodiments described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it would be within the knowledge of one skilled in the art to incorporate such feature, structure, or characteristic into other embodiments, whether or not explicitly described, unless clearly stated to the contrary. That is, the various individual elements described below, even if not explicitly shown in a particular combination, are nevertheless contemplated as being combinable with each other to form other additional embodiments or to complement and/or enrich the described embodiment or embodiments, as would be understood by one of ordinary skill in the art.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to". The term "or" is used herein to mean, and is used interchangeably with, the term "and/or", unless context clearly indicates otherwise.

The term "such as" is used herein to mean, and is used interchangeably, with the phrase "such as but not limited to". Unless specifically stated or obvious from context, as used herein, the term "about" is understood as within a range of normal acceptance in the art, for example within standard deviations of the mean.

What is claimed is:

1. A medical system comprising:
 a medical device configured to generate a first code or coded message; and
 a controller, where the controller is configured to be in electronic communication with the medical device, where the controller comprises a processor and a memory, where the controller is configured to generate a second code or coded message based upon information received from the medical device, where the controller is configured to transmit the second code or coded message to the medical device,
 where the medical device is configured to block the medical device from being used when the first code or coded message and the second code or coded message are not the same or identical.

2. The medical system of claim 1, wherein the controller is further configured to:
 transmit a query to the medical device for the information;
 receive the information from the medical device; and
 generate the second code or coded message according to the information.

3. The medical system of claim 2, wherein the query comprises a software command to request at least one of:
 identifying information which identifies the medical device, or
 status information regarding use of the medical device.

4. The medical system of claim 3, wherein the medical device is further configured to:
 retrieve at least one of the identifying information or the status information from a memory of the medical device; and
 generate the first code or coded message according to the at least one of the identifying information or the status information stored in the memory of the medical device.

5. The medical system of claim 1,
 wherein the medical device is configured to generate the first code or coded message as a hash value according to a hash function; and
 wherein the controller is configured to generate the second code or coded message as the same hash value according to the same hash function.

6. The medical system of claim 5, wherein the information comprises a set of parameters for use with the hash functions comprises at least one of the identifying information which identifies the medical device or the status information regarding use of the medical device.

7. The medical system of claim 1 where the information comprises use information which indicates whether the medical device is new or used, and where the controller is configured to use the use information to generate the second code or coded message.

8. The medical system of claim 7 where the controller is configured to use the use information as a parameter in a hash function to generate the second code or coded message as a hash value.

9. The medical system of claim 8 where the medical device is configured to use the use information as a parameter in a hash function to generate the first code or coded message as a hash value.

10. The medical system of claim 1 where the information comprises identification information which identifies the medical device, and where the controller is configured to use the identification information to generate the second code or coded message.

11. The medical system of claim 10 where the controller is configured to use the identification information as a parameter in a hash function to generate the second code or coded message as a hash value.

12. The medical system of claim 11 where the medical device is configured to use the identification information as a parameter in a hash function to generate the first code or coded message as a hash value.

13. The medical system of claim 1 where the information comprises at least one of:
an amount of time the medical device has been operated,
an amount of time the medical device has been powered up,
a number of activations of an activation switch, or
a number of cycles, rotations, strokes or reciprocations of a motor of the medical device.

14. The medical system of claim 13 where the controller is configured to use the received information as a parameter in a hash function to generate the second code or coded message as a hash value.

15. The medical system of claim 14 where the medical device is configured to use the information as a parameter in a hash function to generate the first code or coded message as a hash value.

16. The medical system of claim 1 where the medical device is configured to compare the first code or coded message to the second code or coded message.

17. The apparatus as in claim 1 where the controller is configured to at least partially store the received information in the memory, and the controller is configured to subsequently compare the stored information to second information received from the medical device when the medical device is unplugged from the controller and subsequently reconnected to the controller.

18. The apparatus as in claim 17 where the controller is configured to determine if the medical device has been used previously based upon parameters including a grace period of time between when the medical device was unplugged and then reconnected.

19. A method comprising:
receiving information from a medical device, where the received information comprises use information regarding prior use of the medical device;
based at least partially on the receiving of the information, transmitting a signal to the medical device, where the signal is configured to be used by the medical device to update the use information stored in the medical device;
generating a coded message based at least partially upon the received information; and
transmitting the coded message to the medical device, where the coded message is configured to be used by the medical device to select an operation of the medical device.

20. The method of claim 19, further comprising:
querying the medical device for information identifying the medical device; and
where the receiving of the information comprises receiving the information identifying the medical device; and
where the information identifying the medical device and/or the use information is used as a parameter for generating the coded message.

21. A method of blocking use of a medical device, the method comprising:
generating, by a controller, a first hash value from a first set of parameters;
generating, by the medical device, a second hash value from the first set of parameters;
determining whether the first hash value and the second hash value are identical; and
controlling operation of the medical device according to the determination of whether the first hash value and the second hash value are identical.

* * * * *